(12) United States Patent
Solecki

(10) Patent No.: US 10,632,233 B2
(45) Date of Patent: Apr. 28, 2020

(54) IMPLANTABLE DEVICE, ESPECIALLY FOR THE RECONSTRUCTION OF THE ABDOMINAL WALL

(71) Applicant: COUSIN BIOTECH, Wervicq Sud (FR)

(72) Inventor: Gilles Solecki, Lannoy (FR)

(73) Assignee: COUSIN BIOTECH, Wervicq Sud (FR)

( * ) Notice: Subject to any disclaimer, the term of this patent is extended or adjusted under 35 U.S.C. 154(b) by 0 days.

(21) Appl. No.: 15/119,740

(22) PCT Filed: Feb. 17, 2015

(86) PCT No.: PCT/FR2015/050383
§ 371 (c)(1),
(2) Date: Aug. 18, 2016

(87) PCT Pub. No.: WO2015/124860
PCT Pub. Date: Aug. 27, 2015

(65) Prior Publication Data
US 2017/0065749 A1    Mar. 9, 2017

(30) Foreign Application Priority Data
Feb. 19, 2014  (FR) ..................... 14 51316

(51) Int. Cl.
*A61L 31/10*   (2006.01)
*A61L 31/14*   (2006.01)
*A61F 2/00*    (2006.01)

(52) U.S. Cl.
CPC ............ *A61L 31/10* (2013.01); *A61F 2/0063* (2013.01); *A61L 31/14* (2013.01); *A61L 31/141* (2013.01);
(Continued)

(58) Field of Classification Search
None
See application file for complete search history.

(56) References Cited

U.S. PATENT DOCUMENTS 6,258,124 B1 *  7/2001  Darois ................. A61F 2/0063
                                                606/151
6,562,363 B1    5/2003  Mantelle
(Continued)

FOREIGN PATENT DOCUMENTS

RU       2460494 C2    9/2012
RU   24604942460494 C2    9/2012
(Continued)

OTHER PUBLICATIONS

International Preliminary Search Report and Written Opinion dated Sep. 1, 2016, International Application No. PCT/FR2015/050383, pp. 1-7 (Including English Translation).
(Continued)

*Primary Examiner* — Carlos A Azpuru
*Assistant Examiner* — Casey S Hagopian
(74) *Attorney, Agent, or Firm* — MH2 Technology Law Group, LLP

(57) ABSTRACT

The present invention relates to an implantable device, in particular for wall repair comprising a reinforcing textile implant having first and second surfaces, a bioadhesive coating to coat said first surface at least in part, said coating comprising at least one ionic, cross-linked bioadhesive polymer selected from among the following polymers: an acrylic acid polymer, methacrylic acid polymer, itaconic acid polymer, maleic acid polymer or maleic anhydride polymer having an adhesive function that can be activated in an aqueous medium.

17 Claims, 1 Drawing Sheet

(52) U.S. Cl.
CPC ... *A61L 31/145* (2013.01); *A61F 2310/00389* (2013.01); *A61L 2420/06* (2013.01); *A61L 2430/30* (2013.01)

(56) References Cited

U.S. PATENT DOCUMENTS

| | | | |
|---|---|---|---|
| 9,320,826 B2 | 4/2016 | Lee | |
| 2002/0082372 A1* | 6/2002 | Leboeuf | A61L 27/34 |
| | | | 526/227 |
| 2007/0129736 A1 | 6/2007 | Solecki | |
| 2010/0137903 A1* | 6/2010 | Lee | A61K 31/765 |
| | | | 606/213 |
| 2010/0305589 A1 | 12/2010 | Solecki | |
| 2011/0158929 A1* | 6/2011 | Kim | A61K 8/8147 |
| | | | 424/70.16 |
| 2013/0103060 A1* | 4/2013 | Stopek | A61F 2/0063 |
| | | | 606/151 |
| 2014/0154328 A1* | 6/2014 | Sovic Brkicic | A61K 9/2081 |
| | | | 424/494 |

FOREIGN PATENT DOCUMENTS

| | | | | |
|---|---|---|---|---|
| RU | 2503430 C1 * | 1/2014 | | |
| RU | 2503430 C1 | 1/2014 | | |
| WO | WO-9403159 A1 * | 2/1994 | | A61K 9/0024 |
| WO | 99/15210 A2 | 4/1999 | | |
| WO | WO-9915210 A2 * | 4/1999 | | A61K 9/0014 |

OTHER PUBLICATIONS

Database CA Chemical Abstracts Service, Columbus, Ohio, US Parshikov, V.V.et al Endoprosthesis for sutureless intra-abdominal plasty in ventral hernias XP002732339.

Database CA Chemical Abstracts Service, Columbus, Ohio, US Abelevich, A.I.et al Endoprosthesis for paracolostomal hernias repair XP002732338.

* cited by examiner

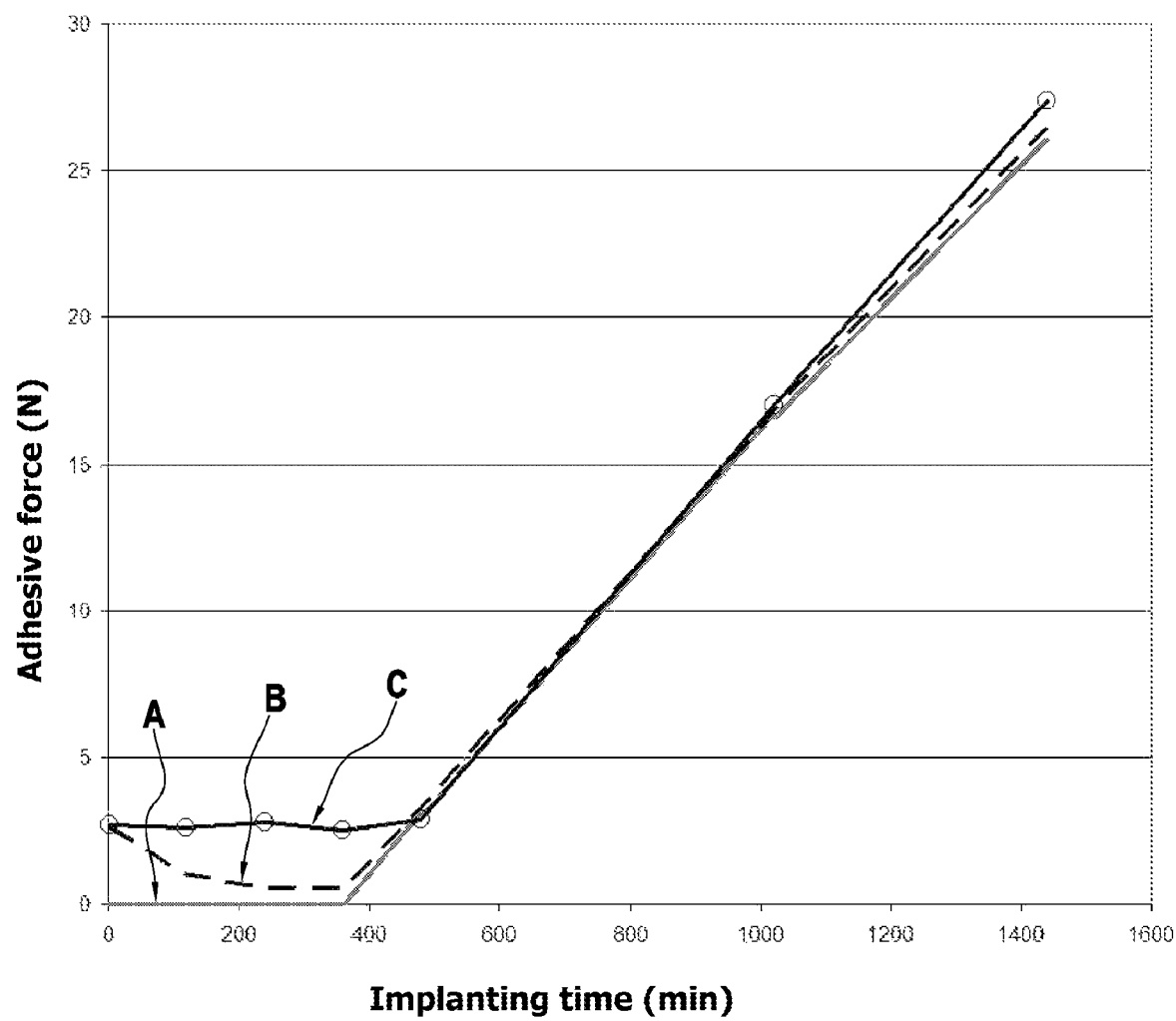

IMPLANTABLE DEVICE, ESPECIALLY FOR THE RECONSTRUCTION OF THE ABDOMINAL WALL

The present invention concerns the technical field of implantable devices intended in particular to repair defects of the abdominal wall such as inguinal hernias and/or abdominal eventration.

The present invention more specifically concerns implantable devices comprising textile reinforcement implants of which one of the surfaces is coated at least in part with a coating comprising an intraoperatively mucoadhesive polymer.

In the meaning of the present invention by intraoperative is meant the period extending from the time when the implantable device is placed in contact with the wall to be reinforced up until several hours after completion of the surgical procedure, in particular about five hours after the completion of said procedure.

BACKGROUND OF THE INVENTION

Document WO 2009/030867 is known describing an implantable device comprising a textile implant having one surface coated at least in part with a coating comprising a polyvinylpyrrolidone polymer and 4 weight % plasticizer relative to the weight of said polymer. For example, said plasticizer is polyethylene glycol. The polyvinylpyrrolidone polymer is not cross-linked and is therefore soluble in contact with the water contained in the body. This coating is mucoadhesive through the creation of weak bonds of Van der Waals type between the coating and the water contained in the mucus covering the abdominal wall to be reinforced. These weak bonds allow repositioning of the prosthesis without degrading the textile implant but this cannot be obtained by the surgeon without loss of adhesion between the textile implant and the abdominal wall to be reinforced. This loss of adhesion may cause migration of the textile implant intraoperatively and subsequent hernia recurrence. It is therefore recommended, but difficult to achieve for a non-experienced surgeon, to position the textile implant just once on the abdominal wall without any subsequent adjustment in particular by causing said textile implant to slide in a plane parallel to said abdominal wall.

In general it is therefore necessary, after positioning the textile implant on the muscle wall to be reinforced, to adjust the position thereof by causing it to slide in a direction parallel to the plane in which it is contained, or by lifting off the implant. This adjustment allows centering of the textile implant on the wall defect.

Yet this implantable device cannot undergo adjustment of position via sliding or detaching after the initial positioning thereof without deteriorating the adhesion forces between the textile implant and the abdominal wall.

A non-exhaustive explanation of this loss of adhesion would be migration of part of the self-adhesive coating on the abdominal wall at the time of adjusting or detaching the implant.

Other types of bio-adhesives are also known composed of monomers which undergo polymerisation intraoperatively, and optionally also cross-linking, and thereby allow attaching of textile implants onto the abdominal wall via covalent bonds. These intraoperative polymerisation reactions, optionally accompanied by cross-linking, have the disadvantage of always being exothermal thereby generating risks of tissue necrosis. These adhesives are usually sprayed either onto the abdominal wall to be reinforced or onto one side of the textile implant at the time of surgical procedure. It is therefore difficult to control the amount of implanted adhesive. These adhesives are often blood derivatives or cyanoacrylate monomers. Once polymerisation is completed, the surgeon no longer has any possibility of repositioning the textile implant on the abdominal wall via sliding without breaking the covalent bonds and hence deteriorating the adhesion forces of the textile implant on the wall. It is therefore necessary, once a textile implant is joined to the abdominal wall to be reinforced via covalent bonds formed between the bioadhesive coating and said wall, that the textile implant must be correctly centered when first positioned on the wall defect without requiring any adjustments which would deteriorate the adhesion force of the textile implant on the abdominal wall.

Document WO 2012/064821 describes an adhesive partly composed of L-3-4-dihydroxyphenylalanine (DOPA) originating from marine mussels. This adhesive can be arranged in the form of a coating on one of the surfaces of a textile implant. The adhesion between the textile implant and the wall to be reinforced is obtained by covalent bonds. On this account, the textile implant cannot be repositioned postoperatively without deteriorating the surface of the textile implant which received the coating and/or deteriorating the adhesion of the implantable device. The adhesion forces involved between the textile implant coated with the bioadhesive coating and the wall to be reinforced are too strong. Example 35 in document WO 2012064821 shows a rupture load of about 5.5+/−0.8 pounds (2.5 kg+/−0.36 kg) to detach the textile implant from a membrane of bovine pericardium. This separation in the vast majority of cases generates rupture of the textile implant. Even if the surgeon manages to detach the textile implant without deteriorating the textile surface of the implant coated with the bioadhesive coating, and without tearing tissues, this detachment is obtained with definitive rupture of the covalent bonds and hence with complete loss of adhesion forces.

The behavior of a foreign material in contact with living tissues has already been closely examined by several authors. With knitted textile prostheses or implants in polypropylene first an acute inflammatory reaction phase is observed that is exudative and then cellular. After wounding of tissue e.g. abdominal surgery, the normal healing process is initiated. It starts by inflammation, first characterized by vasoconstriction and platelet accumulation. Fibrin is then formed to stop haemorrhaging and lasts about 15 minutes. A parallel phenomenon is observed with subsequent exudation of proteins and plasma cells in the affected region. Cell response occurs between 6 h and 16 h after the initial surgical lesion when the onset occurs of a large amount of polymorphonuclear neutrophils corresponding to the first wave of cell migration. They remain for 3 to 5 days with a peak at 68 h. On Day 1 there is already incursion of monocytes. These are macrophage precursors. Fibroblast proliferation starts about 36 h after the surgical lesion. The macrophages are then activated and leukocytes predominate as from Day 3 when they reach a maximum level and persist until complete healing. This first phase lasts up until the $2^{nd}$ day and may last up until post-operative Day 4. These different cells are then progressively replaced by fibroblasts the activity of which intensifies with the production of collagen until total colonisation and ingrowth of the prosthesis in about 4 to 6 weeks. There is therefore a critical period before the fibroblast reaction intensifies. It is especially during this period that the stability of the textile implant must be ensured by securing points. A weak inflammatory reaction reflects biological tolerance whereas the intensity of fibroblast activity is the indication of good resistance via the creation of healing tissue of good quality. In addition, the risk of infection is proportional to local inflammatory reaction. The ideal prosthesis would be the one which causes low inflammatory reaction and intense fibroblast activity. The duration of the inflammatory reaction differs according to authors. For some it disappears in a few weeks, for others it persists several months. This reaction is dependent not only on the material used but also on the texture or porosity thereof. If the primary securing of the textile implant is ensured by surgical sutures or merely by inter-positioning of the implant between the planes of the wall, there is a risk of migration or mobilization of the reinforcement over the days following after the procedure. It is conventionally considered that definitive (secondary) securing obtained by healing and ingrowth of the textile implant in the wall is only acquired after 1 month to 6 weeks.

There is therefore a need for an implantable device, in particular for wall repair, comprising a textile implant coated on one of its surfaces and at least in part with a bioadhesive coating which can be repositioned multiple times without loss of adhesion.

There is also a need for an implantable device for which the amount of bioadhesive coating is able to be controlled and reproducible, in particular a bioadhesive coating which can be stored at the same time as said textile implant in a sterilization pouch and hence able to undergo a sterilization step e.g. with ethylene oxide in the gaseous state.

SUBJECT AND SUMMARY OF THE INVENTION

According to a first aspect, the subject of the invention is therefore an implantable device in particular for wall repair, comprising:
a) a reinforcing textile implant having first and second surfaces; and
b) a bioadhesive coating to coat said first surface at least in part, said coating comprising at least one ionic, cross-linked bioadhesive polymer selected from among the following polymers: an acrylic acid polymer, methacrylic acid polymer, itaconic acid polymer, maleic acid polymer or maleic anhydride polymer having an adhesive function that can be activated in an aqueous medium.

It has been found that the bioadhesive polymer of the invention allows securing of the textile implant, on its surface coated at least in part with said coating, onto a wall to be reinforced in particular an abdominal wall, without loss of adhesion of said device on said wall even if said device has repositioned on said wall simply by sliding or even detached from said wall.

Advantageously, the polymer of the invention is cross-linked so that it is not or only scarcely water-soluble in contact with water contained in the body, which prevents loss of adhesion via dissolution of part of the coating.

In addition, the polymer of the invention adheres to the wall to be reinforced without forming covalent bonds with the latter, or releasing heat, so that it is possible to reposition the device of the invention by sliding or lift-off without deteriorating the abdominal wall or said first surface of the textile implant.

One non-exhaustive explanation is that the bioadhesive coating of the invention adheres via the formation of ionic bonds and/or bonds of Van der Waals type.

The bioadhesive coating of the invention is stable, enabling it to be arranged on the first surface of the textile implant, to undergo a sterilization step, said coated implant being arranged in a sterilization pouch. Advantageously, the surgeon does not have to spray a glue onto the textile implant just prior to procedure. In addition, the amount of coating deposited on the first surface of the textile implant can be controlled during the manufacturing process of the device, which improves reproducibility and reliability of adhesion as well as patient comfort.

In the meaning of the present invention, by textile implant is meant any patch knitted, braided or woven from elongate elements and any patch in one or more nonwovens.

Preferably the textile implant is knitted or woven, more preferably a knit and further particularly a warp knit.

Advantageously, the textile implant comprises pores opening onto the first surface and/or second surface and having a dimension of between 0.5 mm and 4 mm, more advantageously between 0.5 mm and 2 mm, in particular in the order of one millimeter. These pores or orifices may or may not pass through the entire thickness of the textile implant of the present invention. More advantageously these pores fully pass through the textile implant which therefore has an openwork structure.

Advantageously, the second, non-coated surface of said textile implant promotes the development of healing fibrosis and hence fixation of said implant by the body.

Said elongate elements may be monofilament or multi-filament threads, preferably monofilament threads.

In the meaning of the present invention, by nonwoven is meant any sheet of fibers oriented randomly in the longitudinal direction and/or transverse direction.

In one particular embodiment of the present invention, the textile implant of the present invention is a flexible biocompatible polymer and is non-absorbable i.e. it remains permanently in the body, or semi-absorbable i.e. only part of the textile implant remains permanently in the body. The semi-absorbable textile implant is manufactured with absorbable polymer materials and non-absorbable polymer materials. Advantageously, the polymer is a synthetic or semi-synthetic material. Advantageously, if it is non-absorbable, it is selected from among polyethylenes, polyesters, polypropylene, polytetrafluoroethylene (PTFE), polyamide (6/6), polypropylene/PTFE, polyethylene terephthalate. In particular it is polypropylene. If the textile implant is semi-absorbable, the absorbable polymer filament is in the form of D or L lactic acid polymer (PLLA or PDLA) or a copolymer of lactic acid and glycolic acid (PLGA) whilst the non-absorbable polymer filament is selected from among polyethylenes, polyesters, polypropylene, polytetrafluoroethylene (PTFE), polyamide (6/6), polypropylene/PTFE, polyethylene terephthalate. In particular, for example, the semi-absorbable textile implant is composed of absorbable PLLA filament of diameter 0.15 mm and of non-absorbable polymer filament in propylene of diameter 0.1 mm.

If the textile implant is intended for laparoscopic surgery, its dimensions are solely limited by the surgical use thereof since, when rolled up, it must be able to pass through a trocar generally having a diameter of 1 cm or 1.2 cm. In general, implant dimensions in the range of 13*76 mm to 31*41 cm, advantageously 15*15 cm, 15*13 cm or 13*13 cm, in particular 15*15 cm, with a thickness of 0.3 mm to 0.8 mm, are considered to be desirable for ease of surgical handling. In addition, the textile implant can have any geometry required for surgical use, whether with rectangular, square, triangular, circular or oval contour, the only condition being that it is able to be rolled up.

Advantageously, the textile implant of the present invention has a yield strength higher than 16 N/cm for textile implants intended for small inguinal hernias, in particular higher than 32 N/cm for textile implants intended for abdominal eventration. This strength is measured as per standard ASTMD3787 using the Burst Strength test. For this test a ball is used which deforms the textile implant stretched taut on a ring until rupture. The ring diameter is 1 inch (25.4 cm), the ball diameter is 0.38 inch (9.65 mm) with a testing speed of 12 inches/minutes (304.8 mm/minute). The strength obtained is divided by the perimeter of the ring to obtain strength in N/cm.

The bioadhesive coating can be applied to said first surface of the textile implant in the form of a continuous or discontinuous film, in the form of patterns whether or not uniformly distributed e.g. in alternating strips or dots.

The bioadhesive coating can be applied indifferently on the first or second surface of the textile implant.

The adhesive coating can be applied to the first surface of the implant by coating, doctor blade or immersion of the first surface.

In the meaning of the present invention by bio-adhesive coating is meant any coating able to adhere to body tissues, in particular to the abdominal wall.

Preferably, the textile implant has a mass per unit area less than or equal to 50 g/m$^2$, advantageously less than or equal to 40 g/m$^2$, in particular higher than or equal to 10 g/m$^2$, more particularly higher than or equal to 20 g/m$^2$.

Advantageously, the bioadhesive polymer of the invention is a homopolymer.

The bioadhesive polymer of the invention is an ionic polymer, in particular anionic. The increase in pH causes ionization of the carboxylic acid groups and correlatively the swelling of said polymer in gel form.

The bioadhesive polymer of the invention can therefore form ionic complexes with some drugs that are also ionic, cationic in particular, with a view to obtaining extended release thereof over time.

The improved adhering capacity of the bioadhesive polymer of the invention combined with a textile implant, in particular one that is repositionable without loss of adhesion on the abdominal wall, could be accounted for by the fact that said polymer is cross-linked, but also that it has the ability to form ionic bonds with the abdominal wall.

In one variant, the polymer is cross-linked by a cross-linking agent selected from among a sugar or polyalcohol polyalkenyl polyether or a divinyl glycol.

By divinyl glycol is meant 1,5-hexanediene-3,4-diol.

In the meaning of the present invention by polyalcohol is meant any organic compound of formula $C_nH_{2n+2}O_n$ wherein n is between 2 and 30, n being an integer. The alkyl chain of said polyalcohol being saturated, straight-chain or branched.

In one variant, the cross-linking agent is selected from among a sucrose allyl ether or allyl, diallyl, triallyl or tetraallyl pentaerythritol.

By allyl is meant any group of formula —$CH_2$—CH=$CH_2$.

In one variant, the bioadhesive polymer is a carbomer.

Advantageously, it is a homopolymer carbomer, in particular of type A according to the "Pharmacopeia Monograph Compendia Name" in force in the USA after Jan. 1, 2006.

In one variant, the bioadhesive coating is obtained after the polymerisation of a composition comprising at least one monomer selected from among: acrylic acid, methacrylic acid, itaconic acid, maleic acid or maleic anhydride, and a cross-linking agent, the weight proportion of said cross-linking agent relative to the total weight of monomer(s) is higher than 0% and lower than or equal to 4%, more particularly lower than or equal to 3%, further particularly lower than or equal to 2%, advantageously higher than or equal to 0.10%, more advantageously higher than or equal to 1%.

The amount of cross-linking agent is very low, allowing a slightly cross-linked bioadhesive polymer to be obtained that is insoluble in water however.

Preferably, said composition also comprises a solvent e.g. ethyl acetate.

In one variant, the polymer is dehydrated and capable of forming a gel in an aqueous medium.

Advantageously the polymer is not in gel form before implantation. It is therefore dehydrated. As used in the invention, by "dehydrated polymer" is meant a polymer containing less than 1 weight % water relative to the total weight of the polymer. After implantation, the implanting medium being an aqueous medium, the polymer absorbs the water of the aqueous medium and converts to a gel. Advantageously, this polymer does not form a gel under ambient relative humidity less than or equal to 65% relative humidity (RH). Advantageously, the polymer absorbs at least 20 weight % water relative to the total weight of the polymer to form a gel when being implanted.

As used in the present invention, by "gel" is meant any material formed by a polymeric network retaining a liquid. Gels have a common property with solids i.e. the do not flow under their own weight, but they also have a characteristic of liquids i.e. they deform under the effect of certain amount of stress. The "gel state" could in a certain manner be likened to an intermediate state between liquid and solid. In the present invention, the liquid retained by the polymer network is an aqueous solution, water in particular.

Advantageously, the dehydrated polymer is able to form a gel in an aqueous medium at body temperature i.e. at about 36-37° C. Therefore in this particular embodiment the polymer does not form a gel at a temperature lower than 35° C., advantageously lower than or equal to 30° C., and in particular at a temperature close to ambient temperature i.e. 20-25° C.

Advantageously, the dehydrated polymer able to form a gel in an aqueous medium is such that the gel obtained has a water content of at least 20 weight % when fully hydrated at 37° C., advantageously of at least 30 weight %, in particular between 75 and 99 weight %.

In one particular embodiment, the dehydrated polymer forms a gel no later than within 15 minutes after being placed in contact with an aqueous medium i.e. for the case in the present invention no later than 15 minutes after implanting.

In one variant, the Brookfield viscosity of the bioadhesive polymer at 25° C., dispersed at 0.5 weight % in demineralized water at a pH of between 6 and 8, is higher than 4,000 cPoises, preferably lower than 11,000 cPoises.

More particularly, the Brookfield RVT viscosity, 20 rpm, can be measured on a polymer neutralised at a pH between 7.3 and 7.8 and at 0.5 weight % using a paddle blade n°5 in accordance with Lubrizol standard 430-I.

In one variant, the bioadhesive polymer has a carboxylic acid content higher than or equal to 40%, preferably higher than or equal to 50%.

Advantageously, the carboxylic acid content is measured using Lubrizol standard 1318-A.

More particularly, the carboxylic acid content is lower than or equal to 75%, more particularly lower than or equal to 70%.

In one variant, the mass per unit area (g/m²) of the coating is higher than or equal to the mass per unit area of the textile implant (g/m²).

Preferably, the mass per unit area of the coating is higher than or equal to one and a half times the mass per unit area of the textile implant.

In one variant, the coating comprises a plasticizer, preferably selected from among polyalcohols, preferably polyethylene glycol.

As used in the present invention, by polyalcohol is meant any organic compound of formula $C_nH_{2n+2}O_n$ wherein n is between 2 and 30, n being an integer. The alkyl chain of said polyalcohol being saturated, straight-chain or branched.

By "plasticizer" in the present invention is meant any substance, other than water molecules, capable of reducing the glass transition temperature of the polymer of the invention.

The plasticizer of the invention facilitates depositing of the bioadhesive coating on the first surface of the textile implant.

Advantageously, the plasticizer has a weight average molecular weight Mw of between 100 g/mol and 700 g/mol.

In one variant, the textile implant comprises at least one monofilament thread, in polypropylene in particular, having a diameter greater than or equal to 0.10 mm, and smaller than or equal to 0.60 mm, preferably smaller than or equal to 0.30 mm.

According to a second aspect, the subject of the present invention is a device comprising a sterilization pouch comprising the implantable device according to any one of the variants of the preceding embodiments, preferably the textile implant being in a planar configuration.

Advantageously, the bioadhesive coating of the invention can be deposited on the first surface of the textile implant in a sterilization pouch and thus stored until use.

Sterilization can be carried out by subjecting the sterilization pouch comprising the implantable device of the invention to gamma radiation or gaseous ethylene oxide.

Advantageously, said pouch is permeable to gaseous ethylene oxide.

I—Description of a First Protocol Allowing Evaluation of the Adhesive Force of a Textile Implant after Placing in Position and Intraoperative Adjustment, Comprising the Following Steps:

Step 1: The animal is placed on a sterile operating drape under conditions of temperature T=23° C. and relative humidity RH=35%. The animal is then anesthetized via drug injection of Ketamine (10 mg/kg), Azaperone (2 mg/kg) and Atropine (0.05 mg/kg).

Step 2: Using a scalpel a median abdominal incision is made over a length of 20 cm and two other incisions of length 20 cm are made perpendicular to the ends of this incision. These incisions allow the skin and fat layer to be lifted off to access the animal's abdominal wall.

Step 3: The textile implant placed in position is a square of size 7 cm×7 cm. A first end of polyester USP 3-0 thread is knotted in the centre of the textile implant, the other end of the thread comprises a loop of diameter 30 mm which will be attached to a dynamometer after adjusting the textile implant. The textile implant is placed in position on the right abdominal wall of the animal and is left in place for a time of 5 seconds after which it is fully detached. The textile implant is then again placed in position at the same place on the abdominal wall for a time of 5 seconds. Thereafter, it caused to slide via manual traction along its plane over a distance of 2 cm in the direction perpendicular to the axis of the animal. After a time of 2 min, the adhesion force ($F_A$) of the textile implant on the abdominal wall is dynamometrically measured by pulling on the polyester thread. A digital dynamometer of CHATILLON® trademark, model DFE II, is used to perform this measurement.

The animal is then euthanized.

II—Description of a Second Protocol Allowing Evaluation of the Adhesive Force of the Textile Implant after Placing in Position, Adjustment and Determined Implanting Time, Comprising the Following Steps:

Steps 1 and 2 of the first protocol are reproduced.

The applied prosthesis is a square of size 7 cm×7 cm. A first end of polyester USP 3-0 thread is knotted in the center of the prosthesis, the end other of the thread comprises a loop of diameter 30 mm which, after an implanting time, will allow attachment onto a dynamometer. The prosthesis is placed in position on the animal's right abdominal wall and remains in place for a time of 5 seconds before being fully lifted off. The prosthesis then again placed in position at the same place on the abdominal wall for a time of 5 seconds. It is then caused to slide via manual traction along its plane over a distance of 2 cm in the direction perpendicular to the axis of the animal. It is on and after this moment that the implanting time is started to be measured using a chronometer.

The incisions are then closed with suture thread and the animal allowed to regain consciousness.

After a determined period, the animal is again anaesthetized in the operating unit. After removing the suture threads and opening the incisions, the prosthesis is attached to a dynamometer using the polyester USP 3-0 thread to measure adhesive force. It is at this moment that the implanting time is measured and the adhesion force ($F_B$) is recorded using a dynamometer of CHATILLON® trademark, model DFE II.

The animal is then euthanized.

III—Description of an Example of Embodiment of an Implantable Device of the Invention (C) Compared with a Non-coated Textile Implant (A) and with an Implantable Device Comprising a Pvp-based Bioadhesive Coating (B) the Adhesion Forces ($F_A$) and ($F_B$) of which were Evaluated Following the First and Second Protocols Described under Items I and II Respectively.

1—Textile Implant (A) Non-Coated with a Bioadhesive Coating.

The textile implant (A) is a warp knit patch formed with two polypropylene monofilaments of diameter 0.10 mm on a Rachel loom having 28 needles per inch (1 inch=25.4 mm). The basic structure is formed using two guide bars with one full/one empty threading on each bar. Each guide bar carries a monofilament.

The knit weave is as follows:
movement of first bar: 4-2/2-0/2-4/4-6//
movement of second bar: 4-6/6-8/6-4/4-2//

2—Implantable Device (B)

The textile implant is a warp knit patch coated with a bioadhesive coating. The knitted patch is formed by two polypropylene monofilaments of diameter 0.10 mm on a Rachel loom having 28 needles per inch (1 inch=25.4 mm). The basic structure is formed using two guide bars with one full/one empty threading on each bar. Each guide bar carries one monofilament.

The knit weave is as follows:
movement of first bar: 4-2/2-0/2-4/4-6//
movement of second bar: 4-6/6-8/6-4/4-2//

The bioadhesive coating is composed of polyvinylpyrrolidone (PVP) marketed by BASF® under the trade name Kollidon 90® and of polyethylene glycol (PEG) marketed by BASF® under the trade name Lutrol E400®.

The proportions of the different components in implantable device (B) are the following:

Total mass per unit area of implantable device (B): 194.8 g/m$^2$
Mass per unit area of the non-coated textile implant: 35 g/m$^2$
Mass per unit area of the bioadhesive coating: 159.8 g/m$^2$
Mass per unit area of Kollidon 90®: 158 g/m$^2$
Mass per unit area of Lutrol E400: 1.80 g/m$^2$ 3—Implantable Device (C) of the Invention The textile implant is a warp knit patch coated with a bioadhesive coating. The knitted patch is formed by two polypropylene monofilaments of diameter 0.10 mm on a Rachel loom having 28 needles per inch (1 inch=25.4 mm). The basic structure is formed using two guide bars with one full/one empty threading on each bar. Each guide bar carries one monofilament.

The knit weave is the following:
movement of first bar: 4-2/2-0/2-4/4-6//
movement of second bar: 4-6/6-8/6-4/4-2//

The bioadhesive coating is composed of a polyacrylic acid cross-linked with allyl pentaerythritol marketed by Noveon®, and of Polyethylene glycol (PEG) as plasticizer marketed by BASF® under the trade name Lutrol E400®.

The proportions of the different compounds in the implantable device (C) are the following:

Total mass per unit area of the implantable device: 86.5 g/m$^2$
Mass per unit area of the textile implant: 30 g/m$^2$
Mass per unit area of the bioadhesive coating: 56.5 g/m$^2$
Mass per unit area of the polyacrylic acid cross-linked with allyl pentaerythritol: 48.2 g/m$^2$
Mass per unit area of Lutrol E400®: 8.3 g/m$^2$ IV—Description of FIG. 1

FIG. 1, appended hereto, illustrates three curves of adhesion forces $F_A$ and $F_B$ measured for textile implant (A) and the implantable devices (B) and (C) in accordance with protocols I and II performed on a porcine model. The first points measured at 2 min correspond to adhesion force $F_A$, the points measured 2 min after implantation correspond to adhesion forces $F_B$.

V—TEST RESULTS

According to the three curves illustrated FIG. 1, it is observed that for a implantation time of less than 8h00 (480 min), the adhesion forces of implant (A) and of devices (B) and (C) are less than 3 Newtons. For an implantation time of more than 480 min, healing is observed giving way to cell ingrowth of the prosthesis, hence a very distinct increase in the adhesion forces obtained. With the onset of the acute inflammatory reaction, that is exudative and then cellular, the tissue adhesion of textile implant (A) and of devices (B) and (C) increases considerably and linear fashion on and after this moment.

Advantageously, it is observed that the adhesion force of the implantable device (C) is stable and within the range of [2.5; 2.9] Newtons for an implantation time of less than 480 min despite intraoperative repositioning. After 480 min, adhesion is ensured by the phenomena of cellular ingrowth of the textile implant (A) or of the implantable devices (B) and (C) and shows a major, linear increase.

Table 1 summaries the values $F_A$ and $F_B$ obtained for textile implant (A) and implantable devices (B) and (C) derived from FIG. 1.

TABLE 1

| Implantation time (in minutes) | Textile implant (A) | Implantable device (B) | Implantable device (C) |
|---|---|---|---|
| 2 | 0.0 N | 2.6 N | 2.7 N |
| 120 | 0.0 N | 1.0 N | 2.6 N |
| 240 | 0.0 N | 0.5 N | 2.8 N |
| 360 | 0.0 N | 0.5 N | 2.5 N |
| 480 | 3.0 N | 3.3 N | 2.9 N |
| 1020 | 16.6 N | 16.8 N | 17.0 N |
| 1440 | 26.0 N | 26.5 N | 27.4 N |

The invention claimed is:

1. An implantable device, comprising:
a reinforcing textile implant having a first surface and a second surface designed to reinforce a wall of a body; and
a bioadhesive coating coating at least in part said first surface, said bioadhesive coating comprising at least one ionic, cross-linked bioadhesive homopolymer selected from among the following homopolymers: an acrylic acid homopolymer, a methacrylic acid homopolymer, an itaconic acid homopolymer, a maleic acid homopolymer and a maleic anhydride homopolymer;
wherein the ionic, cross-linked bioadhesive homopolymer has an adhesive function that can be activated in an aqueous medium, wherein said implantable device has:
a first state in which the ionic, cross-linked bioadhesive homopolymer is dehydrated, and has no adhesive function; and
a second state in which the ionic, cross-linked bioadhesive homopolymer is hydrated, forms a gel in an aqueous medium and has an adhesive function, and
wherein the adhesive function of the bioadhesive coating is based on the formation of ionic bonds and/or bonds of Van der Waals type between the bioadhesive coating and the wall.

2. The implantable device according to claim 1, wherein the homopolymer is cross-linked by a cross-linking agent selected from among a sugar polyalkenyl polyether, a polyalcohol polyalkenyl polyether and a divinyl glycol.

3. The implantable device according to claim 2, wherein the cross-linking agent is selected from among a sucrose allyl ether and an allyl, diallyl, triallyl or tetraallyl pentaerythritol.

4. The implantable device according to claim 1, wherein the ionic, cross-linked bioadhesive homopolymer is a carbomer.

5. The implantable device according to claim 1, wherein the bioadhesive coating is obtained after the polymerisation of a composition comprising at least one monomer selected from among: acrylic acid, methacrylic acid, itaconic acid, maleic acid anhydride, and a maleic anhydride, and a cross-linking agent,
wherein the weight proportion of said cross-linking agent relative to the total weight of monomer(s) is higher than 0% and lower than or equal to 4%.

6. The implantable device according to claim 1, wherein the Brookfield viscosity of the ionic, cross-linked bioadhesive homopolymer at 25° C., dispersed at 0.5 weight % in demineralised water, at a pH of between 6 and 8, is higher than 4,000 cPoises.

7. The implantable device according to claim 1, wherein the mass per unit area (g/m$^2$) of the coating is higher than or equal to the mass per unit area of the textile implant (g/m$^2$).

8. The implantable device according to claim 1, wherein the coating further comprises a plasticizer.

9. The implantable device according to claim 1, wherein the textile implant comprises at least one monofilament thread, having a diameter greater than or equal to 0.10 mm and smaller than or equal to 0.60 mm.

10. The implantable device according to claim 6, wherein the Brookfield viscosity of the bioadhesive homopolymer at 25° C., dispersed at 0.5 weight % in demineralised water, at a pH of between 6 and 8, is lower than 11,000 cPoises.

11. The implantable device according to claim 8, wherein the coating comprises a polyalcohol plasticizer.

12. The implantable device according to claim 9 wherein the textile implant comprises at least one monofilament thread of polypropylene.

13. The implantation device according to claim 1, wherein the at least one ionic, cross-linked bioadhesive homopolymer has a carboxylic content higher than or equal to 40%.

14. The implantation device according to claim 1, wherein the at least one ionic, cross-linked bioadhesive homopolymer has a carboxylic content higher than or equal to 50%.

15. A device comprising a sterilisation pouch comprising the implantable device according to claim 1.

16. A device according to claim 15 wherein the textile implant is in a planar configuration.

17. The device according to claim 15, wherein the implantation device is sterilized when placed in the sterilization pouch by subjecting the sterilization pouch comprising the implantable device to gamma radiation or gaseous ethylene oxide.

* * * * *